(12) United States Patent
Karlovac et al.

(10) Patent No.: US 11,255,845 B2
(45) Date of Patent: Feb. 22, 2022

(54) DIAGNOSTIC TESTING ASSAYS AND RELATED DEVICES WITH SECURITY AND METHODS OF USE THEREOF

(71) Applicant: Cellmic, LLC, Inglewood, CA (US)

(72) Inventors: Neven Karlovac, Inglewood, CA (US); Onur Mudanyali, Inglewood, CA (US)

(73) Assignee: NOWDiagnostics, Inc., Springdale, AR (US)

( * ) Notice: Subject to any disclaimer, the term of this patent is extended or adjusted under 35 U.S.C. 154(b) by 0 days.

(21) Appl. No.: 15/430,698

(22) Filed: Feb. 13, 2017

(65) Prior Publication Data

US 2018/0164295 A1 Jun. 14, 2018

Related U.S. Application Data

(60) Provisional application No. 62/432,022, filed on Dec. 9, 2016.

(51) Int. Cl.

| | | |
|---|---|---|
| *G01N 33/53* | (2006.01) | |
| *B01L 3/00* | (2006.01) | |
| *G01N 21/84* | (2006.01) | |
| *G01N 33/543* | (2006.01) | |
| *G01N 33/52* | (2006.01) | |
| *G01N 21/64* | (2006.01) | |
| *G01N 33/558* | (2006.01) | |
| *G01N 21/77* | (2006.01) | |

(52) U.S. Cl.
CPC .... *G01N 33/5302* (2013.01); *B01L 3/502715* (2013.01); *G01N 21/6428* (2013.01); *G01N 21/8483* (2013.01); *G01N 33/52* (2013.01); *G01N 33/525* (2013.01); *G01N 33/54386* (2013.01); *G01N 33/54387* (2021.08); *G01N 33/558* (2013.01); *B01L 2200/141* (2013.01); *B01L 2300/168* (2013.01); *G01N 2021/6439* (2013.01); *G01N 2021/7786* (2013.01); *G01N 2201/062* (2013.01)

(58) Field of Classification Search
CPC .... G01N 21/59; G01N 21/6428; G01N 21/17; G01N 21/64; G01N 21/63; G01N 21/62; G01N 33/5302; G01N 33/53; G01N 33/50; G01N 33/48; B01L 3/502715; B01L 3/5027; B01L 3/502; B01L 3/50
USPC .............................................. 422/69; 436/501
See application file for complete search history.

(56) References Cited

U.S. PATENT DOCUMENTS

| | | |
|---|---|---|
| 2005/0123439 A1 | 6/2005 | Patton et al. |
| 2013/0052748 A1 | 2/2013 | Campbell et al. |
| 2015/0056719 A1* | 2/2015 | Karlovac ............... G01N 21/55 436/501 |

FOREIGN PATENT DOCUMENTS

| | | | |
|---|---|---|---|
| WO | WO 0171344 | 9/2001 | |
| WO | WO 2015/004555 A2 * | 1/2015 | ............. G01N 21/84 |

OTHER PUBLICATIONS

PCT/US2017/017623, Search Report and Written Opinion, dated May 10, 2017.

* cited by examiner

*Primary Examiner* — Christine T Mui
(74) *Attorney, Agent, or Firm* — Sandra Poteat Thompson; Finlayson Toffer Roosevelt & Lilly LLP

(57) ABSTRACT

A secure assay device is disclosed herein that provides: an assay or a test device that provides at least one result, wherein the assay or test device comprises at least one surface which exhibits optical change in response to at least one target particle, at least one marker or a combination thereof; and at least one multi-layer coating that at least partially covers the assay membrane, the assay device or a combination thereof, wherein the multi-layer coating blocks or impairs the user visualization of the optical change, the at least one result or a combination thereof. A secure reader and method of utilizing the secure assay device and secure reader are disclosed herein.

15 Claims, 4 Drawing Sheets

A method 700 of providing a confidential in-vitro diagnostic test includes:

providing 710 an assay or a test device that provides at least one result, wherein the assay or test device or comprises at least one surface which exhibits optical change in response to at least one target particle, at least one marker or a combination thereof;

providing 720 at least one multi-layer coating that at least partially covers the assay membrane, the assay device or a combination thereof, wherein the multi-layer coating blocks or impairs the user visualization of the optical change, the at least one result or a combination thereof; and utilizing 730 a reader instrument to obtain test results invisible to the user and to provide results securely and confidentially to others.

*FIG. 7*

DIAGNOSTIC TESTING ASSAYS AND RELATED DEVICES WITH SECURITY AND METHODS OF USE THEREOF

This United States Utility Application claims priority to U.S. Provisional Patent Application Ser. No. 62/432,022 filed on Dec. 9, 2016, which is commonly-owned and incorporated herein in its entirety by reference.

FIELD OF THE SUBJECT MATTER

The field of the subject matter is diagnostic testing assays and layered materials and coating materials that function at least in part to optically encrypt the results of or from diagnostic testing assays and related devices.

BACKGROUND

There are a number ways to test for health conditions and diseases, but in general, tests or assays can be grouped into those that are performed by physicians and health care professionals and those that are performed by the patient. In the latter case, such as in the case of a pregnancy test, the test results are read immediately by the patient and are open to their interpretation. The self-testing and self-evaluation of the results may be convenient for the patient, but it may not be the best approach from a patient well-being or public policy perspective. This is particularly the case for infectious diseases, such as HIV and other STDs (sexually transmitted diseases), along with major health conditions including cancer and pregnancy.

In the case of other types of tests, such as food testing, crop testing, veterinary applications, drugs of abuse testing, bio-defense applications using IVD (in-vitro diagnostics) technologies and immunoassays (lateral flow tests, flow through tests, rapid diagnostics tests, micro-array formats, etc), it may be advantageous to have the results reviewed and interpreted by a third-party company or individual, because of confidentiality issues, misinterpretation issues or issues arising from the test subject hiding or fraudulently reporting the results. In these cases, the test result is required and/or preferred to be analyzed and interpreted first by a third-party individual (e.g., healthcare and laboratory professionals) and/or machine (e.g., readers) to avoid misunderstanding or misinterpretation of test results.

There are currently various types of assays with optical output on the market, including chromatographic, fluorescent, up-converting phosphors and luminescent. Chromatographic assays, which are typically developed using gold, silver, carbon, latex and other visible particles and labels display test results in the form of a change of color, contrast and/or visual intensity. By their very nature, the results of these tests are visible to the user or operator and there is currently no available way to even partially hide the test result from the user or unauthorized operator.

At the same time, there are some methods to indirectly address this issue of test result confidentiality and security but with significant disadvantages. In one type of assays, the user activates the assay using his/her sample (e.g., blood, bodily fluid, etc.) and then is required to send the activated test back to the healthcare facility (laboratory, hospital, doctor's office, etc.) or other facility before the test results become visible. Once the test result is received, it is read either visually or using a digital instrument at this facility. Results are then provided back to the patient or authorized user by written communications or followed by some other action, like a follow up visit to the healthcare provider.

There are several drawbacks to these types of tests. First, the time between the test activation or sample collection by the end user (i.e., patient) and its receipt and analysis by the facility is typically quite long (i.e., up to several days). Immunoassay tests are not stable for extended periods of time and reactions do not stop for several hours, even days. Therefore, these types of tests (e.g., lateral flow assays) are supposed to be interpreted typically within less than 15 minutes, otherwise these tests become invalid, inaccurate and ineffective. Moreover, the environmental conditions are not precisely controlled during the transportation of the activated test/assay, potentially affecting the assay/test result.

Another indirect method is to construct the assay with several different features or patterns which become visible to the user as the test is developed. However, the meaning of those visible features is hidden from the user. To interpret them requires a reader that uses an algorithm to derive the test result; that test result is kept hidden in the reader and confidentially transmitted to the facility. This method works quite well but the need to incorporate in the assay more than one test feature per analyte is a huge disadvantage—it requires more expensive development and generally leads to compromises in test performance.

Alternatively, fluorescent and up-converting phosphor assay technologies are used for security purposes (and also for better sensitivity). The test results are not visible to the naked eye and they can be read only with a special reader using special light sources (e.g., Ultra Violet). However, these fluorescence-based technologies can only offer limited testing applications and fluorescent labels cost significantly more than visible markers (such as commonly-used gold nanoparticles). In addition, they require significantly larger upfront investment in R&D and equipment.

Luminescent assays generate an optical result that is generally too weak to be read visually and requires a sensitive reader. These assays meet the confidentiality requirement; however, it is in their nature that they are available only for limited niche applications.

Rapid diagnostic assays or tests (RDTs) play an important and growing role in the continuum of care worldwide. Administered either at the point of care in doctors' offices, hospitals, urban and remote clinics, or by ambulatory health workers and providing immediate results these tests contribute to improved access, lower cost, and better quality healthcare. An increasing number of RDTs are available for home use by patients and the general public for testing of acute and chronic conditions. The dominant technology used for RDTs is Lateral Flow Immuno-Chromatographic assay (LFI) followed by Lateral Flow Immuno-Fluorescent assays. The worldwide annual value of LFI tests and services of $18B according to BCC Research. RDTs are also available in other variations of immunoassays, such as flow-through and dipstick tests, as well as other chemical or biochemical methods. In fact, contemplated embodiments described here are applicable to any RDT using a change of the optical properties as the mechanism of action. All RDTs typically include an active part which interacts with the analyte in the sample and a surrounding structure; together they form an assay device suitable for handling by the patient or user.

To this end and in order to achieve the goal of confidentiality and security it would be desirable to produce and utilize an assay device that would make it difficult and nontrivial for an end user or operator to visually interpret the test results but would require a specialized reader instrument to securely transmit the results to a testing facility or administrative entity. It would also be desirable to ensure that any solution is cost effective and reliable; and applicable to majority of existing assay technologies with minimal adaptation.

SUMMARY OF THE SUBJECT MATTER

A secure assay device is disclosed herein that provides: an assay or a test device that provides at least one result, wherein the assay or test device comprises at least one surface which exhibits optical change in response to at least one target particle, at least one marker or a combination thereof; and at least one multi-layer coating that at least partially covers the assay membrane, the assay device or a combination thereof, wherein the multi-layer coating blocks or impairs the user visualization of the optical change, the at least one result or a combination thereof.

A secure reader, includes: a set of control electronics, a digital camera component, an illumination component, a housing component, an assay or a test device that provides at least one result, wherein the assay or test device comprises at least one surface which exhibits optical change in response to at least one target particle, at least one marker or a combination thereof; and at least one multi-layer coating that at least partially covers the assay membrane, the assay device or a combination thereof, wherein the multi-layer coating blocks or impairs the user visualization of the optical change, the at least one result or a combination thereof.

Methods of providing a confidential in-vitro diagnostic test include: providing an assay or a test device that provides at least one result, wherein the assay or test device comprises at least one surface which exhibits optical change in response to at least one target particle, at least one marker or a combination thereof; providing at least one multi-layer coating that at least partially covers the assay membrane, the assay device or a combination thereof, wherein the multi-layer coating blocks or impairs the user visualization of the optical change, the at least one result or a combination thereof; and utilizing a reader instrument to obtain test results invisible to the user and to provide results securely and confidentially to others.

BRIEF DESCRIPTION OF THE FIGURES

FIG. 7 shows another contemplated method.

DETAILED DESCRIPTION

Figure 1:
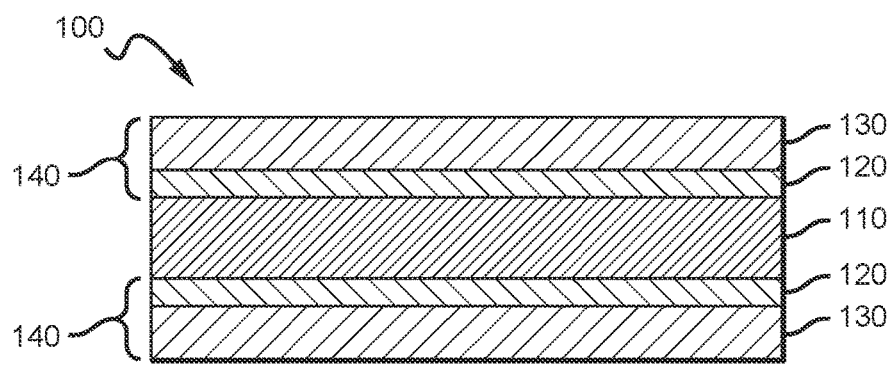
FIG. 1 shows a coating scheme for a contemplated embodiment.

An assay device, which may also be an in-vitro diagnostics assay device, and a reporting instrument has been developed and is described herein that has a rapid diagnostics device, an assay membrane, and a coating material that allows the test results to be securely and accurately reviewed by a third-party physician, health care provider or reviewer. In some embodiments, contemplated test results can be additionally encrypted, such that the patient and general public are protected until the test results can be reviewed and interpreted. Solutions disclosed herein are both cost effective and reliable. Finally, in some instances, the results can be or are automatically transmitted to a testing facility or administrative entity, should that option be desirable for recordkeeping or documentation.

Unlike existing technologies and protocols, contemplated embodiments can be readily applied to any assay that is commercially available or under development. Assay manufacturers and developers can retrofit their technologies with contemplated embodiments. Plastic layers are already widely used in the industry to prevent contamination and one can also replace these layers with contemplated coating or layer or multi-layered coating layers. Therefore, the cost of contemplated embodiments per test is very low, if not zero, to assay manufacturers, those who use assays and those who incorporate assays into reader designs.

Specifically, a secure assay device is disclosed herein that provides: an assay or a test device that provides at least one result, wherein the assay or test device comprises at least one surface which exhibits optical change in response to at least one target particle, at least one marker or a combination thereof; and at least one multi-layer coating that at least partially covers the assay membrane, the assay device or a combination thereof, wherein the multi-layer coating blocks or impairs the user visualization of the optical change, the at least one result or a combination thereof.

As used herein, the phrase "optical change" means that there is a physical change, optical change or a combination thereof, wherein the viewer, user or a device used to analyze the result detects a change in the surface or properties of the surface.

In contemplated embodiments, the at least one target particle, at least one marker or a combination thereof comprises an analyte, an antibody, a molecule, a virus, bacteria, a cell, or a combination thereof.

A secure reader, includes: a set of control electronics, a digital camera component, an illumination component, a housing component, an assay or a test device that provides at least one result, wherein the assay or test device comprises at least one surface which exhibits optical change in response to at least one target particle, at least one marker or a combination thereof; and at least one multi-layer coating that at least partially covers the assay membrane, the assay device or a combination thereof, wherein the multi-layer coating blocks or impairs the user visualization of the optical change, the at least one result or a combination thereof.

Methods of providing a confidential in-vitro diagnostic test include: providing an assay or a test device that provides at least one result, wherein the assay or test device comprises at least one surface which exhibits optical change in response to at least one target particle, at least one marker or a combination thereof; providing at least one multi-layer coating that at least partially covers the assay membrane, the assay device or a combination thereof, wherein the multi-layer coating blocks or impairs the user visualization of the optical change, the at least one result or a combination thereof; and utilizing a reader instrument to obtain test results invisible to the user and to provide results securely and confidentially to others.

In contemplated embodiments, a novel optical technique for safe, secure, and accurate diagnostics using in-vitro diagnostics technologies has been developed. We have also designed the digital read-out system to analyze and interpret the immunoassay, encrypt the test result and automatically share with third-parties.

In order to provide safe, sensitive and accurate diagnostics using in-vitro diagnostics or IVD technologies, the read-out or review should be completed or transmitted after a prescribed time interval, which may be immediately after the test activation (typically 5 to 20 minutes) while at the same time not providing the results to the end user. The integrated read-out instrument (e.g., special reader) can encrypt the test result and automatically share with the healthcare facility (laboratory, hospital, doctor's office, etc.).

Figure 2:
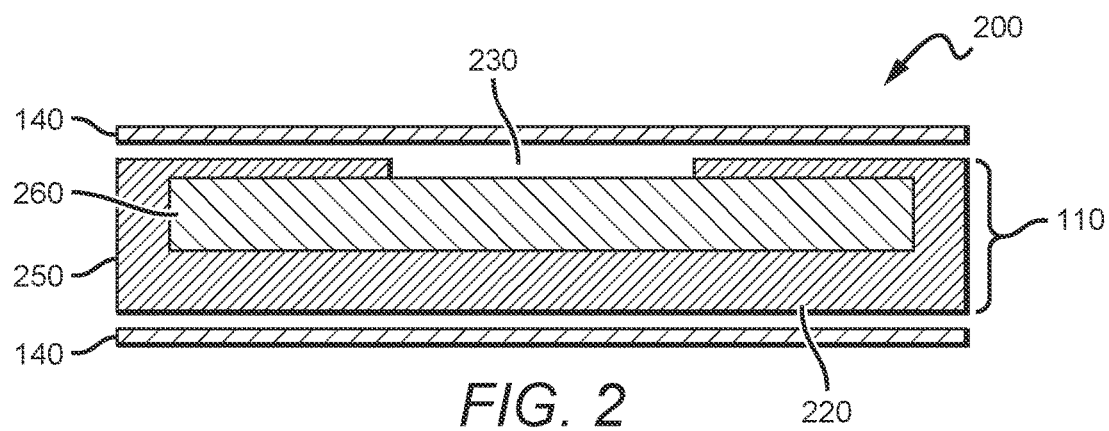
FIG. 2 shows an assay device scheme for a contemplated embodiment.

Specifically, an in-vitro diagnostic testing and assay device 200 has been developed and is shown in FIGS. 1 and 2 that includes an assay membrane 260 and a multi-layer coating 140 that at least partially covers the assay membrane 260, wherein the multi-layer coating or coatings 140 block the user visualization of the test, result or a combination thereof (not shown), such as on the readout side 230. In some optional embodiments, the assay membrane 260 may be enclosed in an outer shell 250. Multi-layer coatings 140 may be placed directly on the assay membrane 260, either as coatings or separate layers, above the assay membrane or on the top of the outer shell 250, and optionally at the bottom 220 of the membrane 260 or shell 250. A contemplated secure assay device which provides confidentiality and security of test results can be referred to by the tradename SECASSAY™. In contemplated embodiments, an assay device may be a fluorescence assay, a microfluidic assay, or a combination thereof.

Figure 3:
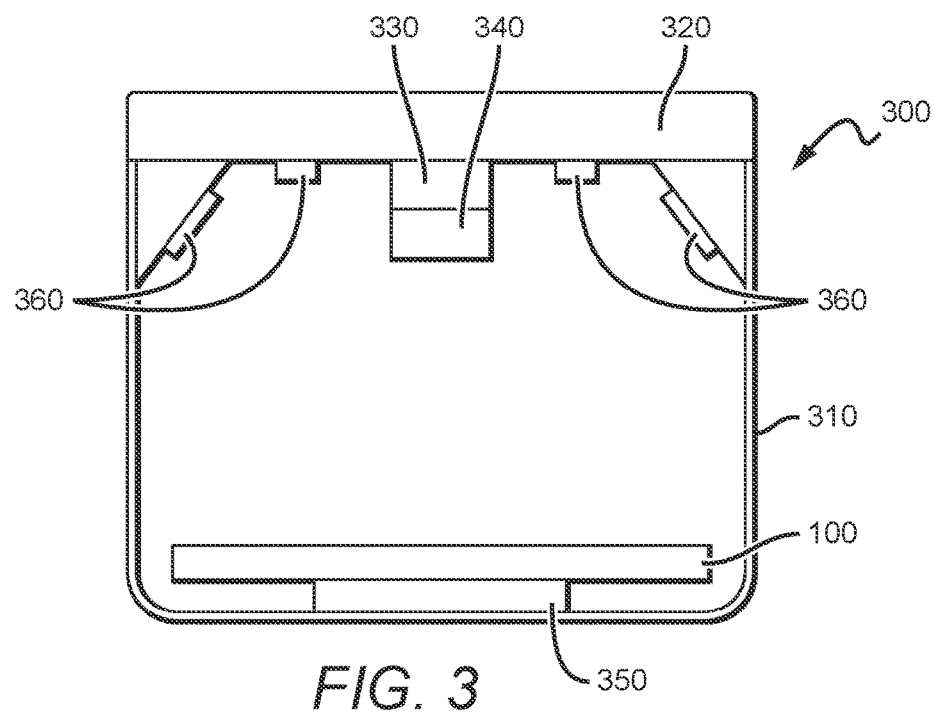
FIG. 3 shows a reader system for contemplated embodiments.
Figure 4:
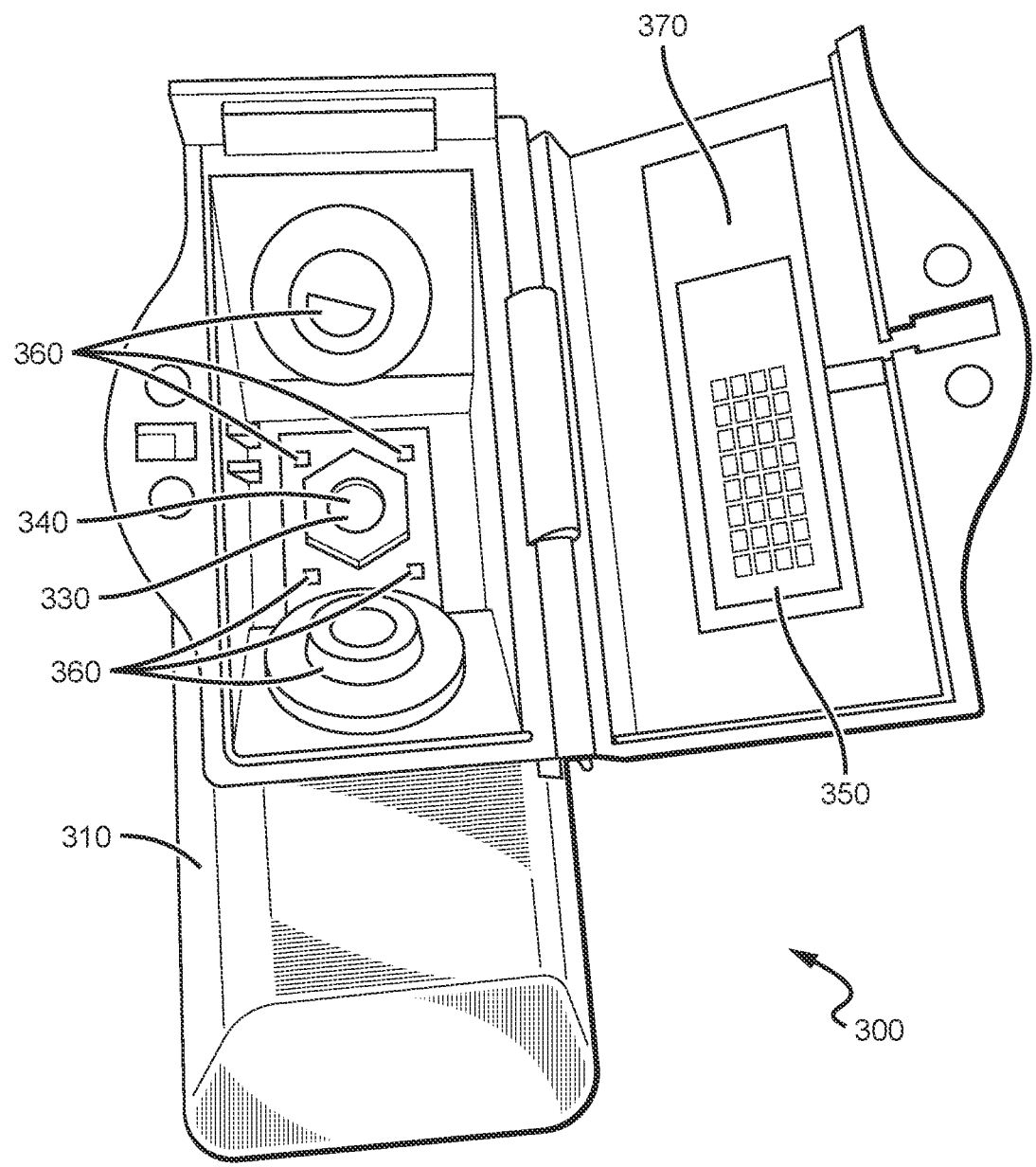
FIG. 4 shows a reader system embodiment.

A secure reader 300 is also disclosed and shown in FIG. 3 and FIG. 4 that includes: a set of control electronics 320, a digital camera component 330, an illumination component 350 and 360, a housing component 310, a rapid diagnostics test tray (not shown in FIG. 3), wherein the tray can hold at least one rapid diagnostics test, like SECASSAY™ or a secure assay device 100, wherein the reader can accommodate more than one different rapid diagnostics test.

A contemplated secure assay device 100, which is shown in FIG. 1 and FIG. 2, containing an assay or test 110 that is located in the test tray (not shown), and a multi-layer coating 140 that at least partially covers the assay 110, wherein the multi-layer coating blocks the user visualization of the test, result or a combination thereof. The digital camera element, shown in FIG. 3 as 330, along with related camera lenses, filters or combination thereof 340, and control electronics 320 can be a part of a cellphone, smartphone, digital camera, other rapid test reader, or other similar device. In contemplated embodiments, a multi-layer coating 140 may be partially reflective, partially transparent, or a combination thereof. In some contemplated embodiments, a multi-layer coating 140 may further comprise layer or layers that are sensitive to light polarization, wavelength, intensity, or a combination thereof.

Contemplated hand-held rapid diagnostics readers may be any suitable reader instrument, including those disclosed in corresponding U.S. application Ser. No. 14/313,615, which is commonly-owned and incorporated herein in its entirety by reference. The key consideration as to whether a reader is suitable is whether it can read the secure assay device 100, as described in the previous paragraph.

In contemplated embodiments, as described earlier, the secure assay devices are designed such that the bottom side is placed above or near the transmission element. The top side is designed so that the active part of the membrane containing test indications is within the field of view of the reader element. The assay membrane, as disclosed herein, is either fully or partially covered with at least one multi-layer coating that has an adjustable transmission. On the bottom side of the coated assay membrane there is a transmission element, such as a light emitting diode or LED. The transmission element transmits light to and through the optional outer shell and through the coated assay membrane.

In some embodiments, contemplated assay membranes comprise a transmission element-facing side and the other side with an active region of interest. The transmission element-facing side is the side of the assay membrane that first comes into contact with the light or energy from the transmission element. The active region of interest side, in these embodiments, is the side of the coated assay membrane that faces the digital camera element (detector) in the reader in order to receive and review the results.

In other embodiments, contemplated assay membranes comprise an active side and an inactive side, which may be next to one another on the same surface side of a contemplated assay membrane. The active side of these contemplated assay membranes is the side that interacts with the reflection or a fluorescent element and at the same time faces the detector, which receives the results. In these embodiments, the reflection or fluorescent element may provide a light or energy that comes at the coated assay membrane from one angle or for a period of time, and then the detector or reader reviews the results from another angle or when the reflection or fluorescent element is no longer active. In these embodiments, the first side may contain or couple with the reflection or fluorescent element and the reader or detector, and the second side may merely bound the inner cavity.

Contemplated visual encryption methods, embodiments and devices rely on multi-layer coating with adjustable transmission that is used to fully (all four sides) or partially (one or more sides) cover the assay membrane or the entire test package (e.g., lateral flow assay, vertical flow immunoassay, flow through assay or other IVD tests), as shown in FIG. 1. FIG. 1 shows a test or assay 110 that has optional band-pass filters and polarizing layers 120 on each side, but it should be understood that they may be on one side or not there at all. In addition, there are partially-reflective/partially transparent coatings 130 on each side, but it should be understood that they may be on one side only. Contemplated reflective or transparent coatings may comprise at least one layer and in some instances more than one layer. These contemplated reflective or transparent coating layers may themselves be multi-layer coatings. These coatings or layered materials are similar to one-way or two-way mirrors.

In some embodiments, an optional polarizer and/or 'wavelength' band-pass filter or layer 120 can be used as the coating layers or in conjunction with the coating layers, which can be optimized per assay type to block, to an increased extent, the user visualization of the test and result.

The partially-reflective, partially-transparent or combination thereof layers can be any material, as long as it satisfies the following principle. When one side of the material is lit or an energy is applied to that side, and the other side is relatively dark or has no significant light or energy present in the space, it allows viewing by an individual or from a detector from the darkened or low energy side but not vice versa.

The optical properties (reflectance and transmittance) can be adjusted by altering the material thickness or the individual layers of materials or composition or density of the coating material depending on the test type, device type, reader or detector type or a combination thereof. These materials may be coated with metals (e.g., silver or gold) and may be widely used in interrogation rooms, security observation decks or security cameras, etc.

In other embodiments, the additional use of polarizer and band-pass filter layers can add an extra level of confidentiality, security or a combination thereof. Because the end users may attempt to read the tests under strong ambient light, sun light or other off-the-shelf light sources, assays can be coated or additionally coated with a special polarization sensitive filter, a band-pass (narrow or wide) filter, or a combination thereof, such that only light or energy with certain polarization and wavelength can pass through the test.

A contemplated reader 300, like the conventional readers disclosed earlier, has three illumination and readout modes: fluorescent 360, reflection 360 and transmission 350, as shown in FIG. 3 and FIG. 4 and works based on recording the image under one or more of these illumination modes or schemes. The reflection mode is used in most available readers as it obviously parallels visual readout, it is easy to implement, and provides comparable results. Each illumination scheme can be customized for illumination angle, different polarization, wavelength, transmission efficiency and light intensity to read the assays that are visually encoded. This optimized read-out system is equivalent to a decoder. The camera system 330 can record the image of the secure assay 100 that becomes digitally visible and process the image to quantify the signal and generates the test result. In FIG. 4, a contemplated secure assay 200 is placed on top of the transmission LEDs 350 as shown by reference number 370.

A contemplated illumination component which illuminates a contemplated secure assay device, illuminates the device from the opposite side of the device from the digital camera component or from the same side as the digital camera component, depending on the needs and design of the reader, assay or combination thereof. In embodiments where the illumination component illuminates the assay device from the same side as the digital camera component, it does so in order to excite the fluorophores and up-converting phosphors in a fluorescent and up-converting phosphor based assay. Contemplated readers comprise an illumination component, which illuminates the secure assay device with a wavelength matched to the multi-layer coating in the secure assay device.

Contemplated approaches can be also applied to fluorescent assays, as contemplated readers and reader solutions utilize an off-axis illumination scheme, and the light reflected by the coating(s) do not reach the camera, whereas the membrane can be excited with partially transmitted excitation light and emit fluorescent signal that can be recorded by the reader system. A contemplated read-out system 300 embodiment is shown in FIG. 3.

Figure 5:
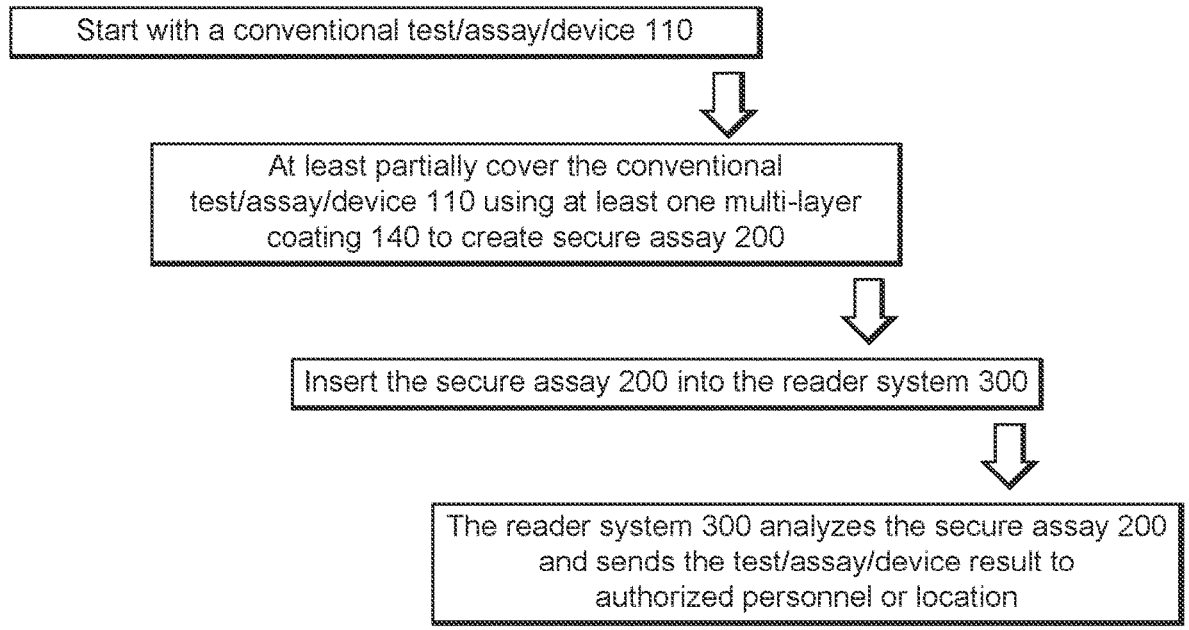
FIG. 5 shows a contemplated method.
Figure 6:
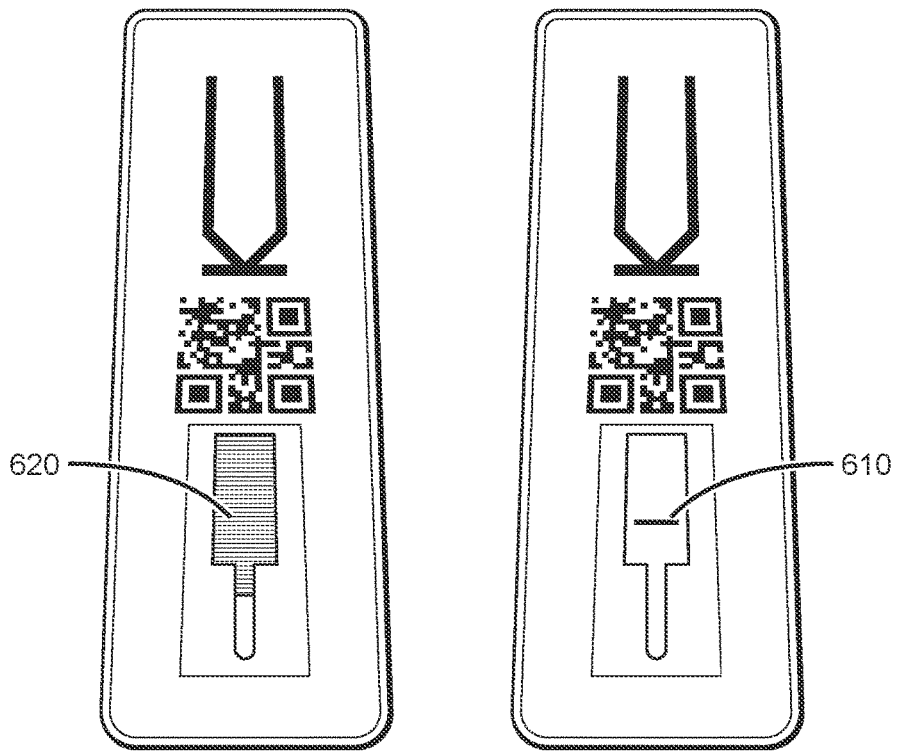
FIG. 6 shows a secure assay as compared with a conventional assay or test.

As shown in FIG. 5, a contemplated method includes starting 510 with a conventional test/assay/device 110, at least partially covering 520 the conventional test/assay/device 110 using at least one multi-layer coating 140 to create a secure assay 200, inserting 530 the secure assay 200 into the reader system 300, and using 540 the reader system 300 to analyze the secure assay 200 and sending the test/assay/device result to authorized personnel or a location (not shown). FIG. 6 shows a conventional assay where the test result is obvious to the viewer 610 and a contemplated embodiment assay where the test result is hidden to the viewer 620.

As shown in FIG. 7, and as discussed earlier, a method 700 of providing a confidential in-vitro diagnostic test includes: providing 710 an assay or a test device that provides at least one result, wherein the assay or test device comprises at least one surface which exhibits optical change in response to at least one target particle, at least one marker or a combination thereof; providing 720 at least one multi-layer coating that at least partially covers the assay membrane, the assay device or a combination thereof, wherein the multi-layer coating blocks or impairs the user visualization of the optical change, the at least one result or a combination thereof; and utilizing 730 a reader instrument to obtain test results invisible to the user and to provide results securely and confidentially to others.

As disclosed and discussed earlier, contemplated embodiments can be readily applied to any assay that is commercially available or under development. Assay manufacturers and developers can retrofit their technologies with contemplated embodiments. Plastic layers are already widely used in the industry to prevent contamination and one can also replace these layers with contemplated coating or multi-layered coating layers. Therefore, the cost of contemplated embodiments per test is very low, if not zero, to assay manufacturers, those who use assays and those who incorporate assays into reader designs.

Thus, specific embodiments, methods of layered and coating materials for diagnostic testing devices have been disclosed. It should be apparent, however, to those skilled in the art that many more modifications besides those already described are possible without departing from the inventive concepts herein. The inventive subject matter, therefore, is not to be restricted except in the spirit of the disclosure herein. Moreover, in interpreting the specification and claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

We claim:

1. A secure assay device, comprising:
   an assay membrane or a test device that provides at least one result, wherein the assay membrane or test device comprises at least one surface which exhibits a change in response to at least one target particle, at least one marker or a combination thereof, wherein the change is illuminated or digitally visible and is recordable by a camera system; and
   at least one multi-layer coating that at least partially covers the assay membrane, the secure assay device or a combination thereof, wherein the multi-layer coating actively blocks or impairs a user visualization of the change, the at least one result or a combination thereof.

2. The secure assay device of claim 1, wherein the at least one target particle, at least one marker or a combination thereof comprises an analyte, an antibody, a molecule, a virus, bacteria, a cell, or a combination thereof.

3. The secure assay device of claim 1, wherein the assay device is a lateral flow and/or vertical flow immunoassay.

4. The secure assay device of claim 1, wherein the assay device is a fluorescence assay.

5. The secure assay device of claim 1, wherein the assay device is a microfluidic device.

6. The secure assay device of claim 1, wherein the multi-layer coating comprises an adjustable transmission.

7. The secure assay device of claim 1, wherein the multi-layer coating is partially reflective.

8. The secure assay device of claim 1, wherein the multi-layer coating is partially transparent.

9. The secure assay device of claim 1, wherein the multi-layer coating further comprises layer or layers that are sensitive to light polarization, wavelength, or intensity.

10. A secure reader, comprising:
    a set of control electronics,
    a digital camera component, an illumination component, a housing component, an assay membrane or a test device that provides at least one result, wherein the assay membrane or test device comprises at least one surface which exhibits a change in response to at least one target particle, at least one marker or a combination thereof, wherein the change is illuminated or digitally visible and is recordable by a camera system; and at least one multi-layer coating that at least partially covers the assay membrane, the secure assay device or a combination thereof, wherein the multi-layer coating actively blocks or impairs a user visualization of the change, the at least one result or a combination thereof.

11. A secure reader of claim 10, comprising an illumination component which illuminates the secure assay device from the opposite side than the digital camera component.

12. A secure reader of claim 10, comprising an illumination component which illuminates the assay device from the same side as the digital camera component.

13. A secure reader of claim 10, comprising an illumination component which illuminates the secure assay device with a wavelength matched to the multi-layer coating in the secure assay device.

14. A secure reader of claim 10, comprising an illumination component which illuminates the secure assay device from the same side as the digital camera component in order to excite a fluorophore and up-converting phosphor in a fluorescent and up-converting phosphor based assay.

15. A method of providing a confidential in-vitro diagnostic test, comprising:

providing an assay membrane or a test device that provides at least one result, wherein the assay membrane or test device comprises at least one surface which exhibits a change in response to at least one target particle, at least one marker or a combination thereof, wherein the change is illuminated or digitally visible and is recordable by a camera system;

providing at least one multi-layer coating that at least partially covers an assay membrane, the assay device or a combination thereof, wherein the multi-layer coating actively blocks or impairs a user visualization of the change, the at least one result or a combination thereof; and utilizing a reader instrument to obtain test results invisible to the user and to provide results securely and confidentially to others.

* * * * *